United States Patent
Giroud et al.

(10) Patent No.: US 6,789,550 B2
(45) Date of Patent: Sep. 14, 2004

(54) PROCESS FOR THE TEMPORARY LIGHTENING OR DYEING OF THE HAIR, AND AEROSOL DEVICE FOR CARRYING OUT THIS PROCESS

(75) Inventors: Franck Giroud, Clichy (FR); Henri Samain, Bièvres (FR)

(73) Assignee: L'Oreal, Paris (FR)

( * ) Notice: Subject to any disclaimer, the term of this patent is extended or adjusted under 35 U.S.C. 154(b) by 268 days.

(21) Appl. No.: 09/907,460

(22) Filed: Sep. 24, 2001

(65) Prior Publication Data

US 2002/0026950 A1 Mar. 7, 2002

(30) Foreign Application Priority Data

Jul. 18, 2000 (FR) ............................................. 00 09407

(51) Int. Cl.$^7$ .............................. A61K 7/13; A61K 7/06
(52) U.S. Cl. ..................................................... 132/208
(58) Field of Search ................................ 132/208, 200, 132/202; 424/401, 70.12, 61, 70, 71, 443, 445, 70.28, 70.13

(56) References Cited

U.S. PATENT DOCUMENTS

| | | | | |
|---|---|---|---|---|
| 4,172,122 A | | 10/1979 | Kubik et al. | 424/59 |
| 5,277,899 A | * | 1/1994 | McCall | 424/71 |
| 5,567,428 A | * | 10/1996 | Hughes | 424/401 |
| 5,593,680 A | | 1/1997 | Bara et al. | 424/501 |
| 6,248,317 B1 | * | 6/2001 | Snyder et al. | 424/70.28 |

FOREIGN PATENT DOCUMENTS

| | | |
|---|---|---|
| EP | 0 761 199 | 3/1997 |
| EP | 0 919 219 | 6/1999 |
| EP | 1 004 288 | 5/2000 |
| FR | 2 382 637 | 9/1978 |
| WO | 98/25710 | 6/1998 |

OTHER PUBLICATIONS

Zviak; Hair Coloring Nonoxidation Coloring; Science of Hair Treatments, Masson, 1988; chapter 7; pp. 235–261.

* cited by examiner

*Primary Examiner*—John J. Wilson
*Assistant Examiner*—Robyn Kieu Doan
(74) *Attorney, Agent, or Firm*—Jacobson Holman PLLC

(57) ABSTRACT

The invention relates to a process for the temporary lightening and/or coloring of the hair, which consists in applying to dry hair by vaporization a lightening solution containing, dissolved in a cosmetically acceptable medium, at least one crystalline hot-melt polymer having a crystal melting point, measured by differential scanning calorimetry, of between 30° C. and 80° C., and at least one cosmetically acceptable volatile solvent having a boiling point of less than 90° C., so as to form, after evaporation of the solvent, a light-colored opaque deposit.

The invention also relates to a device for carrying out this process of temporary lightening and/or coloring of the hair and also to a composition intended to be used in this device.

32 Claims, No Drawings

PROCESS FOR THE TEMPORARY LIGHTENING OR DYEING OF THE HAIR, AND AEROSOL DEVICE FOR CARRYING OUT THIS PROCESS

The present invention relates to a process for the temporary lightening and/or dyeing of the hair by vaporizing a solution of a polymer which forms, after evaporation of the solvent, a light-coloured opaque deposit, to a composition intended to be used in this process and to an aerosol device for carrying out this process.

The bleaching of human keratin fibres, in particular the hair, is generally carried out by oxidation of melanin resulting in the dissolution and partial or total removal of this pigment.

This chemical treatment with oxidizing and alkaline agents is often very harsh and modifies the chemical structure of the keratin, thus resulting in a degradation of the keratin fibres and change in the cosmetic properties of the hair.

The use of oxidizing lightening treatments is moreover relatively long and complex. The final nature of the lightening obtained may appear at first sight to be advantageous. However, the durability of the effect involves, during the regrowth of the hair, renewal of the treatment at regular intervals, thus making this type of treatment fairly restrictive.

A lightening treatment which is practical to use and which would not induce degradation of keratin fibres would consequently constitute a considerable advance in the field of hair treatment.

The Applicant has discovered, quite unexpectedly, that the application to the hair of certain crystalline hot-melt polymers in aerosol form gives rise to the formation of light-coloured opaque polymeric deposits.

The lightening effect thus obtained is temporary since the opaque polymeric deposit may be removed by simply washing the hair. The fugacity of this lightening is an advantage. Specifically, since the simplicity of the treatment and the total absence of degradation of the keratin fibres no longer prohibits multiple applications, the lightening process of the present invention allows great freedom of use. The user may thus vary the intensity and localization of the lightened zones as desired.

Moreover, the addition of colorants or pigments to the lightening solution containing the said crystalline hot-melt polymer makes it possible to obtain coloured shades which the user may combine in total freedom, with each other or with items of his or her wardrobe.

One subject of the present invention is thus a process for the temporary lightening and/or colouring of the hair, which consists in applying to dry hair by vaporization a lightening solution containing, dissolved in a cosmetically acceptable medium, at least one crystalline hot-melt polymer having a crystal melting point, measured by differential scanning calorimetry, of between 30° C. and 80° C., and at least one cosmetically acceptable volatile solvent having a boiling point of less than 90° C., so as to form, after evaporation of the solvent, a light-coloured opaque deposit.

A subject of the invention is also a composition for the temporary lightening and/or colouring of the hair, which composition comprises a lightening solution containing, dissolved in a cosmetically acceptable medium, at least one crystalline hot-melt polymer having a crystal melting point, measured by differential scanning calorimetry, of between 30° C. and 80° C., and at least one cosmetically acceptable volatile solvent having a boiling point of less than 90° C.

Another subject of the present invention is an aerosol device for carrying out the above process of temporary lightening and/or colouring of the hair, this device consisting of a container containing an aerosol composition formed from a propellent compound and a liquid phase which is a lightening solution containing, dissolved in a cosmetically acceptable medium, at least one crystalline hot-melt polymer having a crystal melting point, measured by differential scanning calorimetry, of between 30° C. and 80° C., and at least one cosmetically acceptable volatile solvent having a boiling point of less than 90° C., and of a means for distributing the said aerosol composition, which is suitable to create vaporization conditions for forming a light-coloured opaque deposit.

The present invention thus makes it possible by simple vaporization of a lightening solution onto dry hair, for example using the aerosol device described in greater detail below, to obtain, within a few tens of seconds after evaporation of the solvent, a light, more or less opaque, optionally coloured deposit. The coating thus deposited on the hair has no "powdering" effect, that is to say it does not have the appearance of a powder sprayed onto the hair and shows good resistance to mechanical stresses.

The crystalline hot-melt polymers which may be used according to the present invention for the temporary lightening and/or colouring of the hair are preferably crystalline copolymers comprising i) from 85% to 98% by weight of hydrophobic units and
ii) from 2% to 15% by weight of hydrophilic units.

The hydrophobic units are derived from $\alpha,\beta$-ethylenic monomers containing a $C_{12-50}$ and preferably $C_{12-24}$ n-alkyl side chain, forming crystalline homopolymers known in the literature as side chain crystalline polymers. They are in particular $C_{12-50}$ and preferably $C_{14-24}$ n-alkyl acrylates and methacrylates.

The hydrophilic units are preferably derived from $\alpha,\beta$-unsaturated $C_{3-6}$ monocarboxylic acids such as acrylic acid, methacrylic acid or crotonic acid, unsaturated $C_{4-6}$ dicarboxylic acids such as maleic acid and itaconic acid, or esters and amides containing a $C_{1-4}$ alkyl chain of these monocarboxylic or dicarboxylic acids, such as $C_{1-4}$ alkyl (meth) acrylates and N-($C_{1-4}$ alkyl) (meth)acrylamides.

The synthesis of these polymers is described in particular in international patent application Wo 98/25710.

Hydroxyethyl methacrylate or vinylpyrrolidone may also be used as hydrophilic units.

The carboxylic acid groups of the hydrophilic units are preferably partially or totally neutralized with a base chosen, for example, from sodium hydroxide, potassium hydroxide, 2-amino-2-methylpropanol, monoethanolamine, triethanolamine and triisopropanolamine.

The crystalline hot-melt polymers which may be used in the present invention are moreover characterized by a relatively low crystal melting point, that is to say a melting point of between 30° C. and 80° C. This relatively low melting point allows the polymers to be removed easily by simply washing the hair with water having a temperature above the melting point of the polymer.

The crystal melting point of the polymers which may be used in the present invention is measured by differential scanning calorimetry.

The heat of fusion of a polymer is the amount of energy required to convert a partially or totally crystalline sample into a totally amorphous sample. The thermogram $\Delta Cp=f(T)$, in which $\Delta Cp$ represents the difference in heat capacity of the sample relative to a reference sample which has undergone no thermal transition in the range studied, thus has an endothermal signal whose area is proportional to the heat of fusion of the sample.

The melting point of the crystalline polymers which may be used in the present invention is measured using a differential scanning calorimetry (DSC) machine, model M2920CE-5010 sold by the company TA Instruments. The sample is heated, at a rate of 10° C./minute, from −20° C. to +150° C., and the difference in heat capacity between the sample and the control is recorded as a function of the temperature.

The temperature corresponding to the top of the endothermal peak for fusion of the crystal zones which is thus obtained is known as the crystal melting point ($T_f$).

Mention may be made, by way of example, of crystalline polymers with a low melting point such as those described above, of a copolymer sold under the name Structure® O by the company National Starch. It is a random copolymer consisting of 10% by weight of units derived from acrylic acid and 90% by weight of units derived from n-octadecyl methacrylate. This polymer has a crystal melting point, measured by differential scanning calorimetry, of 46° C.

The hot-melt crystalline polymer(s) described above are applied to the hair in dissolved form in a cosmetically acceptable solvent or mixture of solvents which is volatile enough to allow rapid drying, that is to say drying within a few tens of seconds, of the deposit applied by vaporization.

Solvents having a boiling point, at atmospheric pressure, of less than or equal to 90° C. are preferably used. As examples of solvents which may be used in the present invention, mention may be made of $C_{1-4}$ alcohols such as ethanol or isopropanol, acetone, methyl ethyl ketone, vinyl acetate, methyl acetate, dimethoxyethane and mixtures thereof. Among these solvents, ethanol is preferably used.

The lightening solution may also additionally contain a fraction of one or more cosmetically acceptable solvents having a boiling point of greater than 90° C., such as water, $C_{6-10}$ alkanes, diethoxyethane and ethyl acetate.

In one preferred embodiment of the present invention, this cosmetically acceptable solvent or mixture of solvents represents at least 35% by weight of the lightening solution.

The concentration of the said crystalline hot-melt polymer is preferably between 0.1% and 35% by weight and preferentially between 0.1% and 6% by weight relative to the total weight of the said lightening solution.

According to one particular embodiment of the compositions and of the process of the present invention, the lightening solution also contains one or more colorants or pigments. These colorants or pigments are chosen from those mentioned, for example, in the book by Charles Zviak, Science des traitements capillaires [Science of Hair Treatments], Masson, (1988), chapter 7, or in the Color Index International, 3rd edition.

The lightening solution may also contain one or more additives or adjuvants commonly used in hair compositions. These additives or adjuvants are chosen in particular from thickeners, anionic, nonionic, cationic or amphoteric surfactants, fragrances, preserving agents, sunscreens, proteins, vitamins, provitamins, anionic, nonionic, cationic or amphoteric non-fixing polymers, mineral, plant or synthetic oils, ceramides, pseudoceramides, volatile or non-volatile, linear or cyclic, modified or unmodified silicones, and any other additive conventionally used in cosmetic compositions to be applied to the hair.

The propellent compound is chosen from the compressed or liquefied gases usually used for preparing aerosol compositions. Compressed air, compressed carbon dioxide or compressed nitrogen will preferably be used, or alternatively a gas which is soluble or insoluble in the composition, such as dimethyl ether, hydrocarbons or halo hydrocarbons, in particular fluoro hydrocarbons and mixtures of these compounds.

The aerosol device for carrying out the process of temporary lightening and/or colouring of the hair preferably consists
of a container containing an aerosol composition formed from a propellent compound and a liquid phase, and
of a means for distributing the said aerosol composition giving a solids flow rate of less than or equal to 12 mg/s and a wetting power, at 20 cm, of less than or equal to 100 mg/s.

The distribution means is generally a distribution valve controlled by a distribution head comprising a nozzle via which the aerosol composition is vaporized.

According to the present invention, the "solids flow rate" is understood to mean the amount of dry extract leaving the aerosol device per unit of time. This solids flow rate is expressed in mg/s and is calculated by multiplying the solids concentration in the aerosol composition ($C_S$) by the flow rate of the aerosol composition at the nozzle outlet ($D_{AC}$):

$$D_S = C_S \times D_{AC}$$

The solids concentration in the aerosol composition ($C_S$) expressed in %, corresponds to the amount of solids (in g) relative to 100 g of aerosol composition (liquid phase+propellent compound). The amount of solids is determined after of the spray residue for 1 hour 30 at 105° C.

The flow rate of aerosol composition ($D_{AC}$) corresponds to the amount of aerosol composition (liquid phase+propellent compound) leaving the distribution device per unit of time. It is expressed in mg/s and is determined by measuring the difference between the weight of aerosol before ($M_0$) and after ($M_1$) vaporization for 10 seconds and relating this difference to 1 second:

$$D_{AC} = (M_0 - M_1)/10$$

According to the present invention, the "wetting power" corresponds to the amount of product received by a sheet of plastic placed a distance of 20 cm from the nozzle of the aerosol device, over a given period of time. The product received by the sheet consists of solids, solvent which has not evaporated and possibly propellent compound mixed with the liquid phase.

The wetting power, expressed in mg/s, is measured in the following way: sheet of plastic 21 cm H 23 cm in size is suspended vertically on a precision balance ($1/1000$), the sheet being connected to the balance via the upper edge (generally by means of a balance hook inserted into a perforation placed at the centre of the width and 1 cm from the upper edge of the sheet), and is kept vertical by applying a weight centred on the lower edge (generally by means of a clip fixed to and centred on the lower edge).

A block is placed behind the lower edge of the sheet in order to keep the sheet vertical during impacting of the product.

The aerosol device is placed vertically such that the composition diffusion nozzle is arranged at the centre and 20 cm away from the vertical sheet, to allow vaporization of the product perpendicular to the sheet.

The composition is vaporized for 5 seconds.

The amount of product received on the sheet is measured once the vaporization is complete.

For greater precision, a suitable device comprising a support means for the aerosol device and means for allowing three-dimensional adjustment of the position of the nozzle relative to the vertical sheet may be used. This device may also be equipped with a pneumatic vaporization-duration control device, so as to control the duration of the vaporization precisely. The whole assembly may be controlled by computer.

To avoid any environmental interference, the trajectory of the product between the nozzle and the sheet will advantageously be protected by the walls of a tunnel of suitable size.

Lastly, the product is advantageously vaporized under a controlled atmosphere, preferably at a temperature of 20EC and at a relative humidity of 50%.

The solids flow rate and the wetting power 20 cm from the aerosol device allow the deposition of a sufficient amount of lightening solution.

According to one preferred embodiment of the invention, the aerosol device is suitable for obtaining a solids flow rate of between 2 and 12 mg/s.

According to another preferred embodiment of the invention, the aerosol device is suitable for obtaining a wetting power, at 20 cm, of between 10 and 100 mg/s and preferably between 20 and 80 mg/s.

The solids flow rate and the wetting power of the aerosol device of the invention depend firstly on the aerosol composition and secondly on the distribution means, the two needing to be suitable in order to obtain the desired effect. Among the parameters which may influence these characteristics, mention may be made more particularly of the solids concentration ($C_S$) of the liquid phase, the flow rate of the aerosol composition ($D_{AC}$) and the liquid phase/propellent compound weight ratio.

The solids concentration is advantageously less than or equal to 25% by weight relative to the total weight of the aerosol composition (liquid phase+propellent compound), preferably between 0.04% and 5% by weight and in particular between 0.6% and 3.25% by weight.

The flow rate of the aerosol composition is preferably greater than or equal to 200 mg/s, better still between 200 and 600 mg/s and more preferably between 300 and 400 mg/s.

The aerosol composition is preferably a "long phase", that is to say the liquid phase/propellent compound weight ratio is preferably greater than 1 and more particularly between 1.2 and 3.

A person skilled in the art will know how to select the appropriate distribution means as a function of the aerosol comosition in order to obtain the desired solids flow rate and wetting power characteristics.

The appropriate valves for the particular compositions above are, in particular, valves described in Patent FR 2 382 637 (Abplanalp) and sold under the name Aquasol® by the company Precision. These valves comprise separated channels intended for the liquid products and the propellent compound, in communication via an impact-mixing chamber of the Venturi ejector type in which the flows of product and of propellent compound are introduced freely and come into collision and mix together to form a fine dispersion which is ejected via an orifice. The valves also comprise distribution elements which may be manoeuvred simultaneously by a single member controlling all of the flows.

The valves that are particularly suitable for the present invention comprise:

a nozzle with at least one orifice having a diameter of between 0.40 mm and 0.60 mm, preferably two orifices and more particularly two orifices each having a diameter of 0.5 mm;

an internal restriction of the valve body of between 0.3 mm and 1 mm and preferably between 0.3 mm and 0.6 mm;

a nozzle orifice having a diameter of between 0.3 and 1 mm and preferably between 0.3 and 0.6 mm;

a component in the shape of a disc with two channels of between 0.25 mm×0.25 mm and 0.45 mm×0.54 mm in size, and preferably equal to 0.25 mm×0.25 mm.

A valve with a nozzle having two orifices each having a diameter of 0.5 mm, a valve body with a restriction of 0.36 or 0.58 mm, a nozzle orifice having a diameter of 0.36 mm or 0.60 mm, respectively, and a component in the form of a disc with two channels 0.25 mm×0.25 mm in size, will preferably be used.

Diffusers that are suitable for the compositions of the present invention are, in particular, press-buttons with a whirling nozzle, such as the one sold by the company Precision under the reference 216943-40.

The examples which follow illustrate the invention without, however, limiting its scope.

EXAMPLE 1

The polymer Structure O is dissolved in a mixture of heptane and ethanol (80/20 by weight) to a concentration of 40 g/liter.

65 g of this lightening solution are introduced into an aerosol container fitted with a valve (V36) with a nozzle with two orifices each having a diameter of 0.5 mm, a valve body with a restriction of 0.36 mm, a nozzle orifice having a diameter of 0.36 mm, and a component in the form of a disc with two channels 0.25 mm×0.25 mm in size. 35 g of dimethyl ether are then added as propellent compound and a press-button sold under the reference 216943-40 by the company Precision is fitted on. With this aerosol device, a solids flow rate of 6.5 mg/s and a wetting power, at 20 cm, measured under the conditions described above, of 26 mg/s are obtained.

The lightening solution is sprayed for 10 seconds onto natural dry chestnut-coloured hair. Ten seconds after spraying, the hair appears lightened in colour.

EXAMPLE 2

A coloured lightening solution is prepared by adding to the lightening solution of Example 1 0.1% by weight of a blue colorant (Dianix Blue F2B-SE from the company Dystar) which is fully soluble in the solvent mixture.

This coloured lightening solution is introduced into an aerosol device identical to the one described in Example 1, and is sprayed for 10 seconds onto, natural dry chestnut-coloured hair. About 10 seconds after spraying, the hair appears lightened in colour and has a blue glint.

What is claimed is:

1. A process for the temporary lightening, coloring, or lightening and coloring of hair, comprising spraying a lightening solution onto the dry hair, said lightening solution comprising at least one crystalline hot-melt polymer having a crystal melting point, measured by differential scanning calorimetry, of between 30° C. and 80° C., and at least one cosmetically acceptable volatile solvent having a boiling point of less than 90° C., in a cosmetically acceptable medium, and evaporating the solvent to leave a light-coloured opaque deposit.

2. The process according to claim 1, wherein said hot-melt crystalline polymer comprises i) at least one hydrophobic unit derived from α,β-ethylenic monomers with a $C_{12-50}$ n-alkyl chain side which form crystalline homopolymers, said hydrophobic unit being present in an amount of 85% to 98% by weight, and ii) at least one hydrophilic unit derived from α,β-unsaturated $C_{3-6}$ monocarboxylic acids, unsaturated $C_{4-6}$ dicarboxylic acids, short-chain esters or amides of said monocarboxylic or dicarboxylic acids, hydroxyethyl methacrylate or vinylpyrrolidone, said hydrophilic unit being present in an amount of 2% to 15% by weight.

3. The process according to claim 2, wherein said hot-melt crystalline polymer is a random copolymer comprising about 10% by weight of units derived from acrylic acid and about 90% by weight of units derived from octadecyl methacrylate.

4. The process according to claim 1, wherein said cosmetically acceptable volatile solvent is selected from the group consisting of $C_{1-4}$ alcohols, acetone, methyl ethyl ketone, vinyl acetate, methyl acetate, dimethoxyethane, and mixtures thereof.

5. The process according to claim 4, wherein said volatile solvent is ethanol.

6. The process according to claim 1, wherein the lightening solution further comprises at least one cosmetically acceptable solvent having a boiling point of greater than 90° C.

7. The process according to claim 1, wherein the cosmetically acceptable solvent is present in an amount of at least 35% by weight of the lightening solution.

8. The process according to claim 1, wherein the lightening solution further comprises one or more colorants or pigments.

9. The process according to claim 1, wherein said lightening solution further comprises one or more additives or adjuvants selected from the group consisting of: thickeners; anionic, non-ionic, cationic or amphoteric surfactants; fragrances; preserving agents; sunscreens; proteins; vitamins; provitamins; anionic, nonionic, cationic or amphoteric non-fixing polymers; mineral, plant or synthetic oils; ceramides; pseudoceramides; and volatile or non-volatile, linear or cyclic, modified or unmodified silicones.

10. The process for the temporary lightening, coloring, or lightening and coloring of hair according to claim 1, and further comprising applying said lightening solution to the hair with an aerosol device.

11. A composition for the temporary lightening, coloring, or lightening and coloring of hair, comprising a lightening solution including at least one crystalline hot-melt polymer having a crystal melting point, measured by differential scanning calorimetry, of between 30° C. and 80° C., and at least one cosmetically acceptable volatile solvent having a boiling point of less than 90° C. in a cosmetically acceptable medium.

12. An aerosol device for the temporary lightening, coloring, or lightening and coloring of hair, comprising
 a container containing an aerosol composition formed from a propellent compound and a liquid phase, and
 a means for distributing the aerosol composition, wherein said liquid phase is a lightening solution comprising at least one crystalline hot-melt polymer having a crystal melting point, measured by differential scanning calorimetry, of between 30° C. and 80° C., and at least one cosmetically acceptable volatile solvent having a boiling point of less than 90° C., in a cosmetically acceptable medium, and wherein said distribution means is suitable for obtaining, after evaporation of the solvent, a light-coloured opaque deposit.

13. The aerosol device according to claim 12, wherein said means for distributing the aerosol composition is suitable for obtaining a solids flow rate of less than or equal to 12 mg/s and a wetting power, at 20 cm, of less than or equal to 100 mg/s.

14. The aerosol device according to claim 13, wherein said distribution means is suitable for obtaining a solids flow rate of between 2 and 12 mg/s.

15. The aerosol device according to claim 13, wherein said distribution means is suitable for obtaining a wetting power of between 10 and 100 mg/s.

16. The aerosol device according to claim 13, wherein said distribution means is suitable for obtaining a wetting power of between 20 and 80 mg/s.

17. The aerosol device according to claim 12, wherein said distribution means allows a flow rate of aerosol composition of greater than 200 mg/s.

18. The aerosol device according to claim 12, wherein the solids concentration of the aerosol composition is less than or equal to 25% by weight.

19. The aerosol device according to claim 12, wherein the lightening solution to propellent compound weight ratio is greater than 1.

20. The aerosol device according to claim 12, wherein the hot-melt crystalline polymer comprises
 i) at least one hydrophobic unit derived from $\alpha,\beta$-ethylenic monomers with a $C_{12-50}$ n-alkyl side chain which form crystalline homopolymers, said hydrophobic unit is in an amount of 85% to 98% by weight, and
 ii) at least one hydrophilic unit derived from $\alpha,\beta$-unsaturated $C_{3-6}$ monocarboxylic acids, unsaturated $C_{4-6}$ dicarboxylic acids, short-chain esters and amides of said monocarboxylic or dicarboxylic acids, hydroxyethyl methacrylate, or vinylpyrrolidone, said hydrophilic unit is in an amount of 2% to 15% by weight.

21. The aerosol device according to claim 20, wherein said hot-melt crystalline polymer is a random copolymer comprising about 10% by weight of units derived from acrylic acid and about 90% by weight of units derived from octadecyl methacrylate.

22. The aerosol device according to claim 12, wherein the concentration of said crystalline hot-melt polymer is between 0.1% and 35% by weight relative to the total weight of the lightening solution.

23. The aerosol device according to claim 12, wherein said cosmetically acceptable volatile solvent is selected from the group consisting of C14 alcohols, acetone, methyl ethyl ketone, vinyl acetate, methyl acetate, dimethoxyethane, and mixtures thereof.

24. The aerosol device according to claim 12, wherein the lightening solution further comprises at least one cosmetically acceptable solvent having a boiling point of greater than 90° C.

25. The aerosol device according to claim 12, wherein the fraction of the cosmetically acceptable solvent represents at least 35% by weight of the lightening solution.

26. The aerosol device according to claim 12, wherein the lightening solution further comprises one or more colorants or pigments.

27. The aerosol device according to claim 12, wherein said lightening solution further comprises one or more additives and adjuvants selected from the group consisting of:
 thickeners; anionic, nonionic, cationic or amphoteric surfactants; fragrances; preserving agents; sunscreens; proteins; vitamins; provitamins; anionic, nonionic, cationic or amphoteric non-fixing polymers; mineral, plant or synthetic oils; ceramides; pseudoceramides; and volatile or non-volatile, linear or cyclic, modified or unmodified silicones.

28. The process for the temporary lightening, coloring, or lightening and coloring of hair, which comprises applying the lightening solution to the hair with the aerosol device of claim 12.

29. The aerosol device according to claim 12, wherein said distribution means allows a flow rate of aerosol composition of between 200 and 600 mg/s.

30. The aerosol device according to claim 12, wherein said distribution means allows a flow rate of aerosol composition of between 300 and 400 mg/s.

31. The aerosol device according to claim 12, wherein the solids concentration of the aerosol composition is between 0.4% and 5% by weight.

32. The aerosol device according to claim 12, wherein the solids concentration of the aerosol composition is between 0.6% and 3.25% by weight.

* * * * *